(12) United States Patent
Pusch

(10) Patent No.: US 7,951,101 B2
(45) Date of Patent: May 31, 2011

(54) ADJUSTABLE ORTHOPEDIC AID FOR AN EXTREMITY

(75) Inventor: Martin Pusch, Duderstadt (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 479 days.

(21) Appl. No.: 11/994,489

(22) PCT Filed: Jun. 29, 2006

(86) PCT No.: PCT/DE2006/001129
§ 371 (c)(1),
(2), (4) Date: Jan. 2, 2008

(87) PCT Pub. No.: WO2007/003169
PCT Pub. Date: Jan. 11, 2007

(65) Prior Publication Data
US 2008/0167730 A1    Jul. 10, 2008

(30) Foreign Application Priority Data

Jul. 1, 2005  (DE) .......................... 10 2005 031 185

(51) Int. Cl.
*A61F 5/00* (2006.01)
(52) U.S. Cl. ................. 602/16; 602/20; 602/23; 602/27
(58) Field of Classification Search ...................... 602/16, 602/26–27, 20–23; 128/882
See application file for complete search history.

(56) References Cited

U.S. PATENT DOCUMENTS

| 5,976,063 | A | * | 11/1999 | Joutras et al. | ................. 482/114 |
| 5,980,435 | A | * | 11/1999 | Joutras et al. | ................. 482/114 |
| 2008/0108917 | A1 | * | 5/2008 | Joutras et al. | ................... 601/34 |
| 2008/0108918 | A1 | * | 5/2008 | Joutras et al. | ................... 601/34 |

FOREIGN PATENT DOCUMENTS

| DE | 1291855 | 4/1969 |
| DE | 9104823 | 6/1991 |
| DE | 29601359 | 4/1996 |
| EP | 0449799 | 10/1991 |
| EP | 0663181 | 7/1995 |
| WO | 96/00540 | 6/1994 |
| WO | 2005/048887 | 6/2005 |

OTHER PUBLICATIONS

International Search Report on PCT/DE2006/001129, dated Mar. 3, 2007 (10 pgs).
Article: XP-002425278, "Practical Experiences with the L.A.S.A.R. Posture" Alignment System, Scherer H.W.; (4 pgs). Abstract only in English.
Article: XP-002425277, "Influence of static prosthetic alignment on standing posture and walking in transtibial amputees", S. Blumentritt, S. et al., (8 pgs). Abstract only in English.

* cited by examiner

*Primary Examiner* — Michael A. Brown
(74) *Attorney, Agent, or Firm* — Holland & Hart, LLP

(57) ABSTRACT

An orthopaedic aid for an extremity includes at least one adjustable element for positioning the orthopaedic aid relative to the extremity. The detector arrangement includes a plurality of indicators for indicating torques generated by the detector arrangement. The detector arrangement is positionable such that a section of the detector arrangement is torque-free. The detector arrangement generates torques arising in two opposite directions in a measuring plane in response to deviations from a stable load position.

22 Claims, 2 Drawing Sheets

ADJUSTABLE ORTHOPEDIC AID FOR AN EXTREMITY

This patent application is the national stage of International Application No. PCT/DE2006/001129, which claims priority to German Application No. 10 2005 031 185.7 filed on Jul. 1, 2005 the entire contents of both applications are hereby expressly incorporated by reference.

FIELD OF THE INVENTION

The invention relates to an orthopedic aid, in particular a prosthesis for an extremity, with at least one adjustable attachment for producing a desired orientation.

The adjustment of orthopedic aids, such as orthoses and prostheses, requires particular care, especially where lower extremities are concerned. Prostheses that have not been correctly set can cause considerable lack of balance of the prosthesis wearer and, in the worst case, can even cause falls and resulting injuries.

For the adjustment of orthoses and in particular prostheses, comprehensive measuring devices are known which determine the fit of the orthopedic aid during a stable static load position, by evaluating the forces acting on a support surface and showing these on a suitable display. Such a system is known and in use as LASAR Posture. Unfortunately, such equipment is not always available to orthopedic engineers when making adjustments to orthoses and prostheses.

SUMMARY

In one embodiment, the present invention is an orthopedic aid for attachment to an extremity. The orthopedic aid includes an adjustable element for positioning the aid relative to the extremity and a position detector for indicating the position of the aid relative to the extremity along a load line. The position detector includes at least one lever having a portion that is moveable in a measuring plane upon the application of a torque force to the lever. The position detector also includes at least one force indicator that measures the amount of torque force applied to the lever.

Another embodiment of the present invention is a method of adjusting an orthopedic aid relative to an extremity. The orthopedic aid is positioned relative to the extremity such that one end of a lever is fixed, while a second end of the lever is free to move within a measuring plane. When a load is applied to the orthopedic aid by the extremity along a load line, the torque applied by the extremity is determined by measuring the movement of the free end of the lever. The position of the orthopedic aid relative to the extremity is then adjusted to minimize the torque applied to the lever. Once adjusted, the lever may be locked or fixed in place for normal use.

In another embodiment, the present invention is a detector arrangement which is positioned and designed in such a way that a section is torque-free in the desired orientation and during a stable, static load position in a measuring plane, generates torques in the measuring plane during slight deviations from the stable load position, and comprises indicators for indication of torques arising in two mutually opposite directions in the measuring plane.

The orthopedic aid according to embodiments of the invention permits verification of the desired orientation on the individual patient because the freedom from torque in the measuring plane can be detected by the indicators. No torque is generated in two mutually opposite directions. Torques are generated in both directions in response to any movements outside the stable static load position.

In one embodiment, the detector arrangement has at least one lever that can pivot about a pivot point. The pivot point lies in a load line of the stable load position. The pivot point is optionally positioned at one end of the lever with the other end of the lever being a rotating free end that forms a torque-free section.

The detector arrangement can be securely incorporated into an orthopedic aid. During use of the orthopedic aid, the free end is securely connected by a locking means, for example a locking screw, to a structure of the orthopedic aid. The desired orientation of the orthopedic aid is verified by releasing the locking means. For verification of the desired orientation, the orthopedic aid can be released slightly in order to permit the torque-free section to pivot in the measuring plane in both directions. In the event of correct orientation in the measuring plane, preferably forming the sagittal plane, the free end of the lever is moved neither upward nor downward, but instead catches in a position of balance between limited stops of the released locking means. In the event of slight balancing movements of the patient, such as from slight deviations from the stable static load position which result from balancing movements while standing, a corresponding movement of the free end of the lever takes place in both opposite directions. By contrast, if there is a marked deviation from the desired orientation, such as from an incorrect adjustment of the orthopedic aid, the lever will bear firmly on a limit stop upon release of the locking means. As a result, the incorrect adjustment can be identified. After the adjustment of the orthopedic aid has been corrected, the verification process can be repeated. Once the desired orientation is obtained, the locking means can be actuated and the orthopedic aid can be used in a correct setting.

In an alternative embodiment, the detector arrangement can include two levers with free ends which are connected to each other at a pivot point. The two levers form torque-free sections in the desired orientation during the stable load position. The indicators can in this case be formed by limit stops that counter-act the relative movement of the free ends.

In order to avoid a noticeable movement of the two levers relative to each other, the indicators can be electronic force transducers with which the resulting torques can be measured.

Alternatively or additionally, the indicators can be deformable (e.g., elastic) members, which deform upon contact with the free end of the lever or levers, which can eliminate the need for electronic structural elements and of their energy supply. However, these indicators generally require a noticeable movement of the lever or levers such that the detector arrangement may be designed as an exchangeable adapter, which is fitted into the orthopedic aid only for verification of the desired orientation in place of a structural element of the same size. The adapter can then be fitted into the orthopedic aid in a fixed orientation, in order to check the desired orientation. For use of the orthopedic aid, the structural element of the same size is then installed in place of the adapter.

Various embodiments of the present invention may be used in orthotics and prostheses attached to extremities, including in particular prosthetic feet and knee joints. Certain embodiment could also be used in other orthopedic aids such as hip joints.

BRIEF DESCRIPTION OF THE DRAWINGS

The invention will be explained in more detail below on the basis of illustrative embodiments depicted in the drawing, in which.

DETAILED DESCRIPTION

Figure 1:
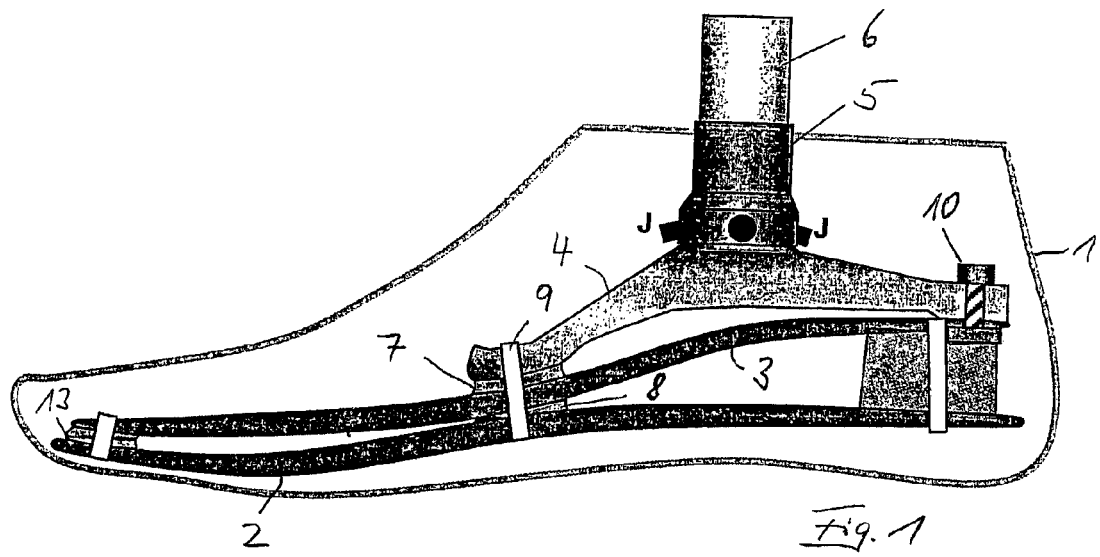
FIG. 1 shows a schematic longitudinal section through an artificial foot, with a detector arrangement secured by a locking screw.
Figure 2:
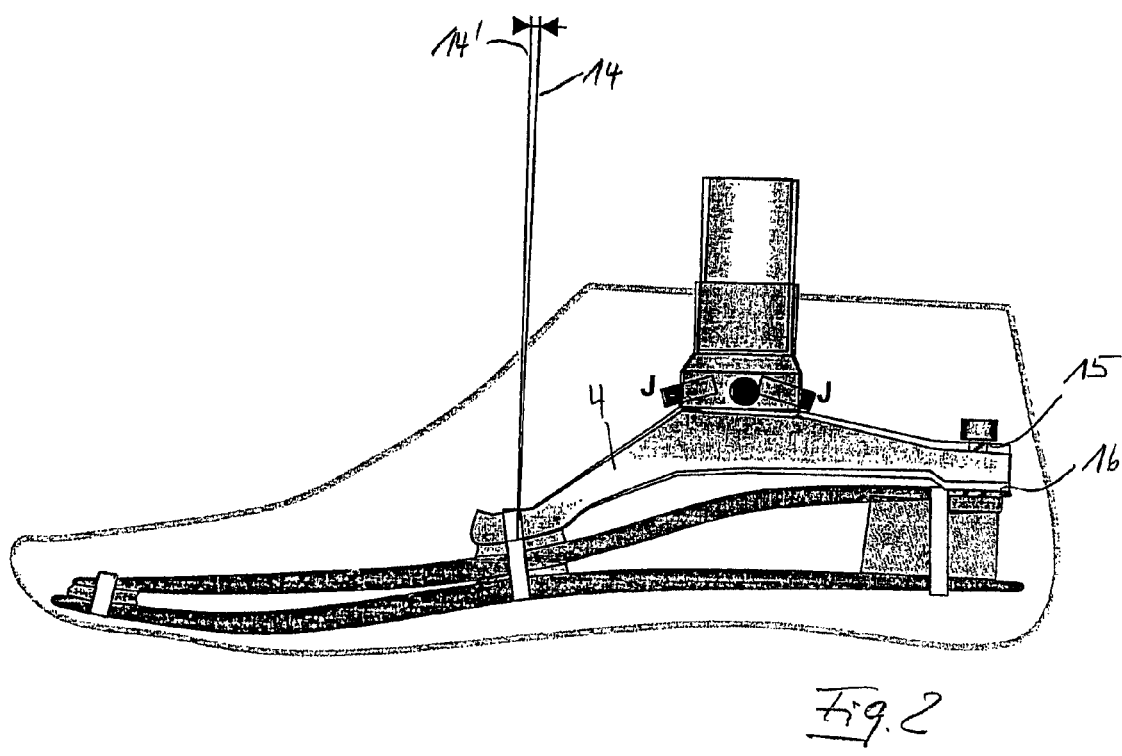
FIG. 2 shows the view according to FIG. 1, with the locking screw released.

FIGS. 1 and 2 illustrate a foot prosthesis 1 whose functional structure is accommodated in a cosmetic envelope forming the contour of the foot. A strip-shaped lower sole spring 2 and, arranged above the latter, a control spring 3, both extend substantially along the length of the foot prosthesis 1. Both springs 2, 3 can be made of a suitable elastic material, for example of a carbon fiber-reinforced plastic. Located above the springs 2, 3, is a generally rigid lever 4, with an adapter 25 (see, e.g., FIG. 4), connected to an adjustment sleeve 5 of a lower leg tube part 6. At the lower end of the adjustment sleeve 5 there are four adjustment screws J with which the position of the adjustment sleeve 5, and thus of the lower leg tube part 6, relative to the foot structure can be adjusted.

The lever 4 extends from a heel end to a front end of the foot prosthesis 1. The lever 4 is connected to the control spring 3 and the sole spring 2 at the approximate foot center, with planar dampers 7, 8 positioned therebetween. A bolt 9 or similar connection means connects the lever 4 and springs 2, 3 such that the lever 4 can execute a pivoting movement relative to the control spring 3 and relative to the sole spring 2, and the control spring 3 can execute a pivoting movement relative to the sole spring 2, in the sagittal plane, such that there is an at least reduced freedom of movement in the frontal plane perpendicular thereto.

At the heel end of the foot prosthesis 1, the lever 4 is connected to the control spring 3 by a locking screw 10 or similar means for preventing movement of the lever. Between the control spring 3 the sole spring 2, a heel damper 11 in the form of an elastic foam block is fitted. When the heel end of the foot 1 is set down, the heel damper 11 is subjected to pressure. When the foot 1 makes a rolling movement over the toe area, the heel damper is subjected to tension. The tensile load is limited by a strap 12 which loops round the outside of the sole spring 2 and the control spring 3 and which does not impede the compression of the heel damper 11, but does limit the elongation of the heel damper 11 under the tensioning action. At the front end in the toe area, the sole spring and the control spring 3 are connected to each other via another damper 13.

In use, when the heel of foot prosthesis 1 is set down, the heel damper 11 is compressed, as a result of which the position of the lower leg tube 6 of a lower leg prosthesis relative to the sole structure 2, 3 pivots rearward causing a desired plantar flexion of the foot relative to the lower leg tube 6. The control spring 3 acts as a two-armed lever whose heel section is pressed down relative to the heel section of the sole spring 2, as a result of which the control spring 3 in the forward area of the foot 1 toward the toe area lifts the sole spring 2 and thus imitates a natural toe movement when the heel is set down, which facilitates the rolling movement of the foot. In the rolling movement of the foot past the stand phase, the sole spring 2, convexly shaped on the underside, is loaded in the forward area of the foot, such that the sole spring 2 in the heel area is pressed down relative to the lever 4, as a result of which the heel damper 11 is relieved or subjected to tensioning. This load is limited by the strap 12.

The adjustment feature of the illustrated foot prosthesis 1 is based on the fact that the dampers 7, 8 and the bolt 9 form a pivot point between the lever 4 and the springs 2, 3, which is located in a perpendicular load line 14 of the patient when standing, as is shown in FIG. 2. Accordingly, the center of gravity of the patient is located perpendicularly above the pivot point. If the center of gravity of the patient is not perpendicularly above the pivot point but instead forms an angle with the latter, as is illustrated for the load line 14', a torque is exerted on the lever 4 such that the lever 4 presses with its free end against the upper head of the screw 10. If, by contrast, the load line 14 is located perpendicularly above the pivot point, the heel end of the lever 4 is unloaded such that the lever 4 is free of torque relative to the pivot point.

Accordingly, To check the correct adjustment of the lower leg tube 6 relative to the lever 4, the locking screw 10 is loosened, such that the heel end of the lever 4 is afforded a vertical range of movement that is limited by an upper limit stop 15, formed by the screw head 10, and a lower limit stop 16, formed here by the heel end of the control spring 3. If the perpendicular load line 14 is located perpendicularly above the pivot point the heel end of the lever 4 is unloaded and can therefore assume a balance position within the range of movement limited by the limit stops 15, 16. By contrast, if the load line 14' enters the pivot point 7, 8, 9 at an angle to the perpendicular, the lever 4 is subjected to a torque which, in the case of the load line 14', presses the heel end of the lever 4 against the upper limit stop 15. The free heel end of the lever 4 will therefore remain on the upper limit stop 15 in the event of a corresponding incorrect adjustment, even if the patient when standing makes the usual balance compensation movements. In this manner, the lever 4 acts as a position detector or detector arrangement. The limit stops 15, 16 may also act to provide a visual or electronic measure of the torque force to allow proper adjustment of the leg tube 6.

By contrast, if the adjustment is correct, such that the center of gravity is located within the perpendicular load line 14, the balance compensation movements of the patient lead to a movement of the heal end of the lever 4 between the upper limit stop and the lower limit stop, as is known from a lever balance. The balance compensation movements, which take place forward and backward in the saggital plane (i.e., in one or two mutually opposite directions in a measuring plane), can be detected from a corresponding upward and downward movement of the heal end of the lever 4 in the movement range, if the adjustment is made correctly. Thus, when the foot prosthesis is correctly positioned relative to an extremity of the patient to which the foot prosthesis is mounted, the lever is free of torque in the measuring plane (e.g., the heal end of the lever 4 is in the movement range). Otherwise, the free end of the lever 4 remains on the one of the limit stops 15, 16, because of the incorrect adjustment. Thus, the locking screw 10 with upper and lower limits stops 15, 16 may operate as force indicators and be used to indicate the occurrence of torque in one or two mutually opposite directions in a measuring plane (e.g., the saggital plane).

When the correct adjustment has been established, the locking screw 10 can be tightened in order to produce a firm connection of the lever 4 to the sole structure 2, 3 and to ensure that the patient does not experience any feeling of imbalance, during walking, as a result of play within the foot structure.

Figure 3:
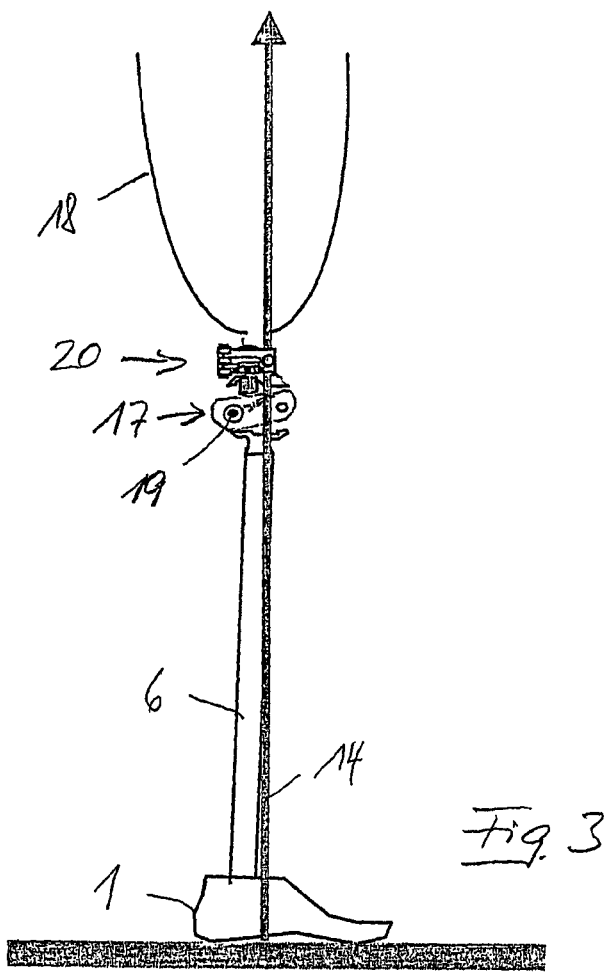
FIG. 3 shows a schematic representation of a prosthesis with a detector arrangement above a knee joint.
Figure 4:
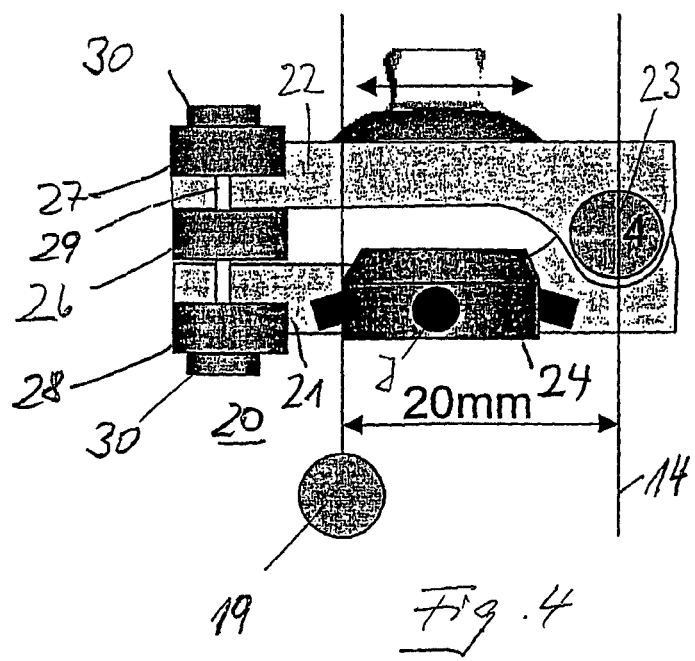
FIG. 4 shows a detail of the detector arrangement according to FIG. 3.

Another illustrative embodiment is shown in FIGS. 3 and 4. These show the cosmetic envelope 1 of a foot prosthesis and the adjoining lower leg tube 6. Arranged at the upper end of the lower leg tube 6 there is an artificial knee joint 17, which connects the lower leg tube part 6 to a receiving funnel 18 for a thigh stump of the patient. FIG. 3 indicates the perpendicular load line 14 intended to pass through the center of gravity of the patient in the sagittal plane. As shown, the perpendicular load line 14 passes a small distance (e.g., approximately 20 mm) in front of a pivot axis 19 of the knee joint. If used in conjunction with the foot 1 shown in FIGS. 1 and 2, the perpendicular load line 14 may also pass through the pivot point previously described.

The knee joint 17 is connected securely to the receiving funnel 18 via a securing adapter (not shown). The securing adapter can be equipped with additional functions. To check the adjustment of the prosthesis arrangement, a detector arrangement 20 is fitted between the knee joint 17 and the receiving funnel 18. The detector arrangement has a lower lever 21 and an upper lever 22, which are connected to each other at their front ends via a pivot hinge 23. The lower lever is provided with an adapter bushing 24 with adjustment screws J, in order to produce an adjustable attachment to the lower leg tube part, which is provided on the upper face with an adapter with truncated cone surfaces. The upper lever 22 extends parallel to the lower lever 21 and is provided on its upper face with an adapter 25 via which the receiving funnel 18, provided on the underside with an adapter bushing part (corresponding to 24) for connection to the adapter 25, can be adjustably attached.

The pivot hinge 23 between the two levers 21, 22 is arranged in such a way that it is located in the perpendicular load line 14. The free ends of the levers 21, 22 are connected to each other via an interposed central damper 26, an upper damper 27 mounted externally on the upper lever 22, and an outer damper 28 mounted on the lower lever 21 A tensioning arrangement 29 with outer contact disks 30 holds the arrangement together such that the dampers 26, 27, 28 are contacted, but not compressed. If the pivot hinge 23 is located with the pivot axis in the perpendicular load line 14, the free ends of the levers 21, 22 are free of force, such that the dampers 26, 27, 28 remain uncompressed.

By contrast, if the perpendicular load line 14 is arranged dorsally from (i.e., behind) the pivot hinge 23 because of an incorrect adjustment, the two levers 21, 22 are pressed against each other at their free ends, such that the central damper 26 is compressed. The compression, leading to a deformation of the central damper 26, is easily detectable, such that the central damper 26 serves as an indicator of a rearward shifting of the perpendicular load line 14.

By contrast, if the load line 14 is located in front of the pivot hinge 23, this results in a torque that presses the free ends of the levers 21, 22 away from each other, such that the outer dampers 27, 28 are compressed, and thus deformed. The outer dampers 27, 28 thus serve as indicators of a forward shifting of the load line 14 from the ideal state.

It will be readily apparent that the dampers 26, 28 can be replaced by electronic force transducers (voltage transducers, acceleration transducers) in order to determine the torques acting on the levers 21, 22. Since these electronic force transducers operate with measurement paths that are imperceptible, such a detector arrangement can remain in the prosthesis during its normal use, since the measurement arrangement does not lead to play in the prosthesis arrangement.

The simpler and more economical design of the detector arrangement with the dampers 26 to 28 requires, by contrast, the replacement of the detector arrangement by an adapter insert for normal use of the prosthesis arrangement.

In one simple embodiment, the pivot hinge 23 can also be formed by a solid hinge. The indicators can in this case also be formed by switches.

The invention claimed is:

1. An orthopedic aid for attachment to an extremity, comprising:
   an adjustment element for adjustably positioning the aid relative to the extremity;
   a position detector for indicating the position of the aid relative to the extremity, the position detector including:
      at least one lever positioned with respect to the extremity such that a portion of the lever is moveable in a measuring plane upon the application of a torque force to the lever caused by the extremity, wherein the lever is free of torque in the measuring plane when the aid is correctly positioned relative to the extremity; and
      at least one force indicator to indicate the occurrence of torque in one or two mutually opposite directions in the measuring plane.

2. The orthopedic aid of claim 1, wherein the lever includes a first portion which is fixed with respect to the measuring plane and a second portion which is moveable in the measuring plane.

3. The orthopedic aid of claim 2 wherein the first portion includes a pivot point about which the second portion moves in the measuring plane upon the application of the torque force.

4. The orthopedic aid of claim 3 wherein the pivot point is positionable perpendicular to a load line formed by the extremity relative to the orthopaedic aid such that substantially no torque force is applied to the lever.

5. The orthopedic aid of claim 4, wherein when the pivot point is not positioned perpendicular to the load line, a torque force is applied to the lever.

6. The orthopedic aid of claim 3, wherein the first portion includes a rotating portion that rotates about the pivot point upon the application of the torque force.

7. The orthopedic aid of claim 1 wherein the at least one force indicator is positioned relative to the lever to limit movement of the lever upon the application of the torque force.

8. The orthopedic aid of claim 7 further including a plurality of force indicators positioned to limit movement of the lever in opposing directions in the measuring plane.

9. The orthopedic aid of claim 1 wherein the force indicators include electronic force transducers.

10. The orthopedic aid of claim 1 wherein the force indicators include deformable elements.

11. The orthopedic aid of claim 1 further comprising a locking element for preventing movement of the lever in the measuring plane.

12. The orthopedic aid of claim 1 wherein the position detector includes at least two levers having respective first portions which are fixed with respect to the measuring plane and respective second portions which are moveable in opposing directions in the measuring plane.

13. The orthopedic aid of claim 1 comprising movement indicators disposed adjacent an upper and lower surface of the second portions of the first and second levers.

14. The orthopedic aid of claim 1 wherein the orthopedic aid is a foot prosthesis, and the first portion of the lever is connected to at least one spring that forms the sole of the foot.

15. The orthopedic aid of claim 1 wherein the orthopedic aid includes a prosthetic knee joint.

16. A method of adjusting an orthopedic aid relative to an extremity comprising:

positioning an orthopedic aid relative to the extremity, the orthopedic aid including at least one lever having a fixed end, and a free end which pivots relative to the free end along a measuring plane upon the application of a torque force;

positioning the extremity to apply a load to the orthopedic aid along a load line;

measuring the torque applied to the lever by the load based on the movement of the free end in the measuring plane;

adjusting the position of the orthopedic aid relative to the extremity to minimize the amount of applied torque caused by the load; and fixing the free-end of the lever from movement after adjustment and prior to using the orthopedic.

17. The method of claim 16, wherein measuring the amount of torque includes measuring an amount of deformation of a plurality of dampers positioned adjacent the at least one lever.

18. The method of claim 16, wherein measuring the amount of torque comprises measuring a deviation of the pivot joint from the load line.

19. The method of claim 16, wherein adjusting the position of the orthopedic aid includes aligning the pivot joint of the at least one lever relative to the load line of the extremity.

20. An orthopedic aid for attachment to an extremity, comprising:
    an adjustment element for adjustably positioning the aid relative to the extremity;
    a position detector for indicating the position of the aid relative to the extremity, the position detector including:
        at least one lever positioned with respect to the extremity such that a portion of the lever is moveable in a measuring plane upon the application of a torque force to the lever caused by the extremity; and
        at least one force indicator that is adapted to measure movement of the lever in the measuring plane;
    wherein the orthopedic aid is a foot prosthesis, and the first portion of the lever is connected to at least one spring that forms the sole of the foot.

21. The orthopedic aid of claim 20, wherein the lever includes a first portion which is fixed with respect to the measuring plane and a second portion which is moveable in the measuring plane.

22. The orthopedic aid of claim 21 wherein the first portion includes a pivot point about which the second portion moves in the measuring plane upon the application of the torque force.

* * * * *